United States Patent
Riteau et al.

(10) Patent No.: US 8,802,623 B2
(45) Date of Patent: Aug. 12, 2014

(54) PAR-1 ANTAGONISTS FOR USE IN THE TREATMENT OR PREVENTION OF INFLUENZA VIRUS TYPE A INFECTIONS

(75) Inventors: Béatrice Riteau, Beynes (FR); Khaled Khoufache, Jouy en Josas (FR)

(73) Assignee: Institut National de la Recherche Agronomique, Paris (FR)

( * ) Notice: Subject to any disclaimer, the term of this patent is extended or adjusted under 35 U.S.C. 154(b) by 0 days.

(21) Appl. No.: 13/508,301

(22) PCT Filed: Nov. 15, 2010

(86) PCT No.: PCT/EP2010/067516
§ 371 (c)(1),
(2), (4) Date: May 4, 2012

(87) PCT Pub. No.: WO2011/058183
PCT Pub. Date: May 19, 2011

(65) Prior Publication Data
US 2012/0213802 A1 Aug. 23, 2012

(30) Foreign Application Priority Data
Nov. 16, 2009 (EP) .................................. 09306098

(51) Int. Cl.
*A61K 31/517* (2006.01)
*A61K 38/04* (2006.01)
*A61K 39/42* (2006.01)
*A61P 31/16* (2006.01)
*A61K 38/00* (2006.01)
*C07K 7/06* (2006.01)
*C07K 14/005* (2006.01)

(52) U.S. Cl.
CPC ...................................... *A61K 38/04* (2013.01)
USPC .......................................... 514/2.4; 514/3.7

(58) Field of Classification Search
None
See application file for complete search history.

(56) References Cited

U.S. PATENT DOCUMENTS

| 5,866,681 A | 2/1999 | Scarborough |
| 2008/0097385 A1* | 4/2008 | Vinten-Johansen et al. .. 604/509 |
| 2012/0058127 A1 | 3/2012 | Vergnolle et al. |

FOREIGN PATENT DOCUMENTS

| WO | 93/18141 | 9/1993 |
| WO | 01/00659 | 1/2001 |
| WO | 2010/128016 | 11/2010 |

OTHER PUBLICATIONS

Couch, "Prevention and treatment of influenza," Drug Therapy 343:1778-1787 (2000).*
Lan et al., "Altered expression and in vivo lung function of protease-activated receptors during influenza A virus infection in mice," Brit. J. Pharmacol. 129:63-70 (2000).*
Feld et al., "Agonists of Proteinase-Activated Receptor-2 Enhance IFN-Gamma-Inducible Effects on Human Monocytes: Role in Influenza A Infection," J. Immunol., 180(10):6903-6910 (2008).
Khoufache et al., "Protective Role for 1-8 Protease-Activated Receptor-2 Against Influenza Virus Pathogenesis Via an IFN-Gamma-Dependent Pathway," J. Immunol., 182(12):7795-7802 (2009).
Lan et al., "Altered Expression and in Vivo Lung Function of Protease-Activated Receptors During Influenza Virus A Infection in Mice," Am. J. Physiol., 286:L388-L398 (2004).
LeBouder et al., "Annexin II Incorporated into Influenza Virus Particles Supports Virus Replication by Converting Plasminogen into Plasmin," J. Virol., 82(14):6820-6828 (2008).
Riteau et al., "Trypsin increases pseudorabies virus production through activation of the ERK signalling pathway," J Gen. Virol., 87(5):1109-1112 (2006).
Steinhoff et al., "Proteinase-Activated Receptors: Transducers of Proteinase-Mediated Signaling in Inflammation and Immune Response," Endocrine Reviews, 26(1):1-43 (2005).
Vergnolle, "Proteinase-activated receptors (PARs) in infection and inflammation in the gut," Int. J. Biochem. Cell Biol., 40:1219-1227 (2008).

* cited by examiner

*Primary Examiner* — Christina Bradley
*Assistant Examiner* — Kristina M Hellman
(74) *Attorney, Agent, or Firm* — McAndrews, Held & Malloy Ltd.

(57) ABSTRACT

The present invention provides methods and compositions (such as pharmaceutical compositions) comprising PAR1 antagonists for treating or preventing influenza virus type A infections, in particular H1N1 infection. PAR1 antagonists may be combined with a PAR2 agonist.

6 Claims, 6 Drawing Sheets

SEQUENCE LISTING

```
<160> NUMBER OF SEQ ID NOS: 8

<210> SEQ ID NO 1
<211> LENGTH: 14
<212> TYPE: PRT
<213> ORGANISM: homo sapiens

<400> SEQUENCE: 1

Ser Phe Leu Leu Arg Asn Pro Asn Asp Lys Tyr Glu Pro Phe
1               5                   10

<210> SEQ ID NO 2
<211> LENGTH: 9
<212> TYPE: PRT
<213> ORGANISM: homo sapiens

<400> SEQUENCE: 2

Ser Phe Leu Leu Arg Asn Pro Asn Asp
1               5

<210> SEQ ID NO 3
<211> LENGTH: 9
<212> TYPE: PRT
<213> ORGANISM: homo sapiens

<400> SEQUENCE: 3

Asn Pro Asn Asp Lys Tyr Glu Pro Phe
1               5

<210> SEQ ID NO 4
<211> LENGTH: 26
<212> TYPE: PRT
<213> ORGANISM: Rattus norvegicus

<400> SEQUENCE: 4

Gly Arg Ala Val Tyr Leu Asn Lys Ser Arg Phe Pro Pro Met Pro Pro
1               5                   10                  15

Pro Pro Phe Ile Ser Glu Asp Ala Ser Gly
            20                  25

<210> SEQ ID NO 5
<211> LENGTH: 6
<212> TYPE: PRT
<213> ORGANISM: artificial
<220> FEATURE:
<223> OTHER INFORMATION: PAR2 activating peptide
```

```
<400> SEQUENCE: 5

Ser Leu Ile Gly Arg Leu
1               5

<210> SEQ ID NO 6
<211> LENGTH: 6
<212> TYPE: PRT
<213> ORGANISM: artificial
<220> FEATURE:
<223> OTHER INFORMATION: PAR2 activating peptide

<400> SEQUENCE: 6

Ser Leu Ile Gly Lys Val
1               5

<210> SEQ ID NO 7
<211> LENGTH: 5
<212> TYPE: PRT
<213> ORGANISM: artificial
<220> FEATURE:
<223> OTHER INFORMATION: PAR1- agonist peptide

<400> SEQUENCE: 7

Thr Phe Leu Leu Arg
1               5

<210> SEQ ID NO 8
<211> LENGTH: 5
<212> TYPE: PRT
<213> ORGANISM: artificial
<220> FEATURE:
<223> OTHER INFORMATION: PAR1- agonist peptide

<400> SEQUENCE: 8

Phe Thr Leu Leu Arg
1               5
```

PAR-1 ANTAGONISTS FOR USE IN THE TREATMENT OR PREVENTION OF INFLUENZA VIRUS TYPE A INFECTIONS

CROSS-REFERENCE TO RELATED APPLICATIONS

This application is a U.S. National Stage application of international application PCT/EP2010/067516, filed in English on Nov. 15, 2010, which designates the United States, and which claims the benefit of EP09306098.6, filed in English on Nov. 16, 2009. Each of these applications is incorporated by reference herein in its entirety.

FIELD OF THE INVENTION

The present invention provides methods and compositions (such as pharmaceutical compositions) for treating or preventing influenza virus type A infections.

BACKGROUND OF THE INVENTION

Epidemic viral infections are responsible for significant worldwide loss of life and income in human illnesses ranging from the common cold to life-threatening influenza, West Nile and HIV infections. Timely detection, diagnosis and treatment are key in limiting spread of disease in epidemic, pandemic and epizootic settings. In particular, prophylactic and therapeutic agents that rapidly inhibit viral assembly and propagation are particularly useful in treatment regimens.

Influenza virus of type A (IAV) causes acute respiratory infections that are highly contagious and afflict humans and animals with significant morbidity and mortality. Thus, there is a need in the clinical arts for new and improved anti-viral medicinal agents. This invention meets these needs.

Activation of host innate immune system aims at controlling the spreading and deleterious effects of IAV infection. However, excessive inflammatory response, due to a dysregulation of cytokine release and strong recruitment of neutrophils at the site of infection, may also mediate severe lung inflammation and increased pathogenesis of IAV. Cytokine dysregulation during IAV infection is thus often associated with fatal outcome of IAV.

The sites of virus replication in the respiratory tract represent complex microenvironments, in which extracellular proteases are present in large amounts. Some of these proteases (trypsin, tryptase) can play a role both in virus replication (Riteau B. et al. 2006; LeBouder F. et al. 2008) and innate immune responses as they are important mediators of inflammatory processes through the activation of a family of receptors called Protease-Activated Receptors (PARs) (Steinhoff M. et al. 2005; Vergnolle N. et al. 2008).

To date four PARs, activated by different proteases, have been cloned (PAR1-4). After cleavage of the receptor by proteases, the newly released amino-terminal sequence binds and activates internally the receptor.

The role of PAR1 in lung IAV infection has never been documented. However elevated PAR levels of pAR1 have been observed in the airways of IAV-infected mice (Lan R S. et al. 2004), suggesting a role for this receptor in the pathogenesis of viral disease. The specific role for PAR1 activation/inactivation in vivo or in vitro has never been addressed.

SUMMARY OF THE INVENTION

The invention relates to a PAR1 antagonist for use in the treatment or prevention of an influenza virus type A infection.

BRIEF DESCRIPTION OF THE DRAWINGS

FIGS. 1 B, C and D: PAR1 agonists modulate cytokines released in epithelial cells. A549 were infected with IAV A/PR/8/34 and treated or not with the PAR1 agonist peptide. After the indicated times post-infection, the release of the indicated cytokines was determined by classical ELISA.

FIG. 2 C: PAR1 agonists increase virus replication in vivo. Mice were infected with IAV A/PR/8/34 (50 pfu or 500 pfu/mice) and treated or not with the PAR1 agonist peptide. IAV virus titers in the lungs were analysed at the indicated time post-infection by classical plaque assay.

FIG. 3 C: PAR1 antagonist SCH79797 inhibits virus replication in vivo. Mice were infected with IAV A/PR/8/34 (50 pfu or 500 pfu/mice) and treated or not with the PAR1 antagonist SCH79797. IAV virus titers in the lungs were then analysed at the indicated time post-infection by classical plaque assay.

DETAILED DESCRIPTION OF THE INVENTION

Figure 1A:
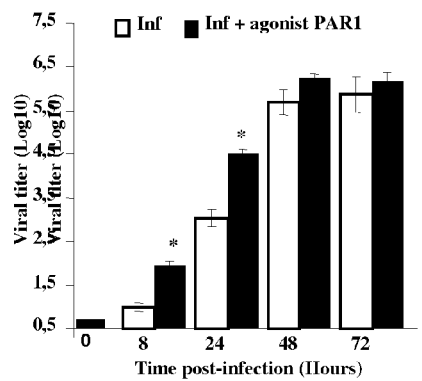
FIG. 1 A: PAR1 agonists increase virus replication in epithelial cells. A549 were infected with IAV A/PR/8/34 and treated or not with the PAR1 agonist peptide. After the indicated times post-infection, the infectious virus titers in the culture supernatants were determined by plaque assay.

The present invention provides methods and compositions (such as pharmaceutical compositions) for treating or preventing influenza virus type A infections.

The inventors indeed investigated the role of PAR1 in influenza pathogenesis in vitro and in vivo. In vitro, stimulation of PAR1 on epithelial cells increased influenza virus type A (IAV) replication. In vivo, stimulation of PAR1 using specific agonists was deleterious in IAV-induced acute lung injury and death. This effect correlated with modification of cytokine release. More importantly, blocking PAR1 with antagonist of PAR1 protected mice from IAV induced death. These results have been found significative.

Accordingly, a first aspect of the invention relates to a PAR1 antagonist for use in the treatment or prevention of an influenza virus type A infection.

As used herein, the term "influenza virus type A infection" refers to any infection caused by an influenza virus type A without consideration of serotype based on hemagglutinine (H1 to H15) and neuraminidase (N1 to N9) expression. Exemplary influenza virus type A that are contemplated by the invention include but are not limited to H1N1, H2N2, H3N2, H5N1, H7N7, H1N2, H9N2, H7N2, H7N3, and H10N7. In a preferred embodiment influenza virus type according to the present invention is H1N1.

In its broadest meaning, the term "treating" or "treatment" refers to reversing, alleviating, inhibiting the progress of influenza virus type A infection, preferably inhibiting the influenza virus type A proliferation. In particular, "prevention" or "prophylactic treatment" of influenza virus type A infections may refer to the administration of the compounds of the present invention that prevent the symptoms of influenza virus type A infections.

The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

In prophylactic applications, compositions containing the antagonist of PAR1 are administered to a patient not already suffering from influenza virus type A infection. Rather, they are directed to a subject who is at the risk of, or has a predisposition, to developing such a disorder. Such applications allow the subject to enhance the patient's resistance or to retard the progression of a from influenza virus type A infection.

As used herein, the term "protease activated receptor-1," "proteinase activated receptor-1" or "PAR1" or "PAR-1" interchangeably refer to a G-protein-coupled receptor that is activated by thrombin cleavage thereby exposing an N-terminal tethered ligand. PAR1 is also known as "thrombin receptor" and "coagulation factor II receptor precursor." See, for example, Vu, et al., Cell (1991) 64(6): 1057-68; Coughlin, et al, J Clin Invest (1992) 89(2):35I-55; and GenBank Accession number NM_001992. Intramolecular binding of the tethered ligand to the extracellular domain of PAR 1 elicits intracellular signaling and calcium flux. See, for example, Traynelis and Trejo, Curr Opin Hematol (2007) 14(3):230-5; and Hollenberg, et al, Can J Physiol Pharmacol. (1997) 75(7):832-41.

The term may include naturally occurring PAR1 and variants and modified forms thereof. The PAR1 can be from any source, but typically is a mammalian (e.g., human and non-human primate PAR1, particularly a human PAR1.

The nucleotide and amino acid sequences of PAR1 are known in the art. See, for example, Vu, et al., Cell (1991) 64(6): 1057-68; Coughlin, et al, J Clin Invest (1992) 89(2): 351-55; and GenBank Accession number NM_001992. The nucleic acid sequence of human PAR1 is published as GenBank accession number NM_001 992 {see also, M62424.1 and gi45O3636). The amino acid sequence of human PAR1 is published as NP_001 983 and AAA36743.

The term "antagonist," as used herein, refers to an agent that is capable of specifically binding and inhibiting signaling through a receptor to fully block or detectably inhibit a response mediated by the receptor. For example, as used herein the term "PAR1 antagonist" is n natural or synthetic compound which binds and inactivates fully or partially PAR1 for initiating a pathway signalling and further biological processes. PAR-1 antagonistic activity may assessed by various known methods. In some cases, a PAR1 antagonist can be identified by its ability to bind to PAR1 and inhibit thrombin-induced calcium flux or thrombin-induced IL-8 production subsequent to intracellular signaling from a PAR1 (e.g., as measured in a FlipR assay, or by ELISA). Additional assays are described by Kawabata, et al., J Pharmacol Exp Ther. (1999) 288(1):358-70. Inhibition occurs when PAR1 intracellular signaling, as measured for example by calcium flux or IL-8 production, from a PAR1 exposed to an antagonist of the invention is at least about 10% less, for example, at least about 25%, 50%, 75% less, or totally inhibited, in comparison to intracellular signaling from a control PAR1 not exposed to an antagonist. A control PAR1 can be exposed to no antibody or antigen binding molecule, an antibody or antigen binding molecule that specifically binds to another antigen, or an anti-PAR1 antibody or antigen binding molecule known not to function as an antagonist. An "antibody antagonist" refers to the situation where the antagonist is an inhibiting antibody.

In one embodiment, a PAR1 antagonist according to the invention may be a peptide, a peptide mimetic, a small molecule organic compound, an aptamer, a pepducin, a polynucleotide or an antibody.

In an embodiment of the invention, the administered PAR1 antagonist inhibits a PAR1 signaling activity. Some of these methods employ a PAR1 antagonist which is a peptidomimetic, e.g., RWJ-56110 or ([alpha]S)-W-[(1S)-3-amino-1-[[{phenylmethyl)amino]carbonyl]propyl]-[alpha]-[[[[[1-(2,6-dichlorophenyl)methyl]-3-(1-pyrrolidinylmethyl)-1H-indol-6-yi]amino]carbonyl]amino]-3,4-difluorobenzenepropanamide.

In another embodiment of the invention, a PAR1 antagonist is a small molecule organic compound. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da. In a preferred embodiment, the PAR1 antagonist is the small organic molecule SCH-79797, which is (N3-cyclopropyl-7-{[4-(1-methylethyl)phenyl]methyl-7H-pyrrolo[3,2-f]quinazoline-1,3-diamine.

In another embodiment of the invention, a PAR1 antagonist is an antagonist PAR1 antibodies or antigen-binding molecule. As used herein, unless otherwise defined, the term "antibody" includes both polyclonal and monoclonal antibodies, as well as antibody fragments having specific binding affinity for their antigen, including, but not limited to, Fv fragments, Fab fragments, Fab' fragments, F(ab)'2 fragments, and single chain (sFv) engineered antibody molecules. The term further includes, unless specifically excluded, chimeric and humanized antibodies, as well as human antibodies in circumstances where such antibodies can be produced.

These anti-PAR1 agents are capable of antagonizing PAR1 mediated signaling activities, e.g., PAR1 mediated interleukin secretion. General methods for preparation of monoclonal or polyclonal antibodies are well known in the art. See, e.g., Harlow & Lane, Using Antibodies, A Laboratory Manual, Cold Spring Harbor Laboratory Press, Cold Spring Harbor, N.Y., 1998; Kohler & Milstein, Nature 256:495-497 (1975); Kozbor et al., Immunology Today 4:72 (1983); and Cole et al., pp. 77-96 in Monoclonal Antibodies and Cancer Therapy, 1985.

In addition, specific PAR1 antagonist antibodies have been disclosed in the art. See, e.g., R. R. Vassallo, Jr. et al. "Structure-Function Relationships in the Activation of Platelet Thrombin Receptors by Receptor-Derived Peptides," J. Biol. Chem. 267:6081-6085 (1992) ("Vassallo, Jr. et al. (1992))"; L. F. Brass et al., "Structure and Function of the Human Platelet Thrombin Receptor," J. Biol. Chem. 267: 13795-13798 (1992) ("Brass et al. (1992)"); and R. Kaufmann et al., "Investigation of PAR-1-Type Thrombin Receptors in Rat Glioma C6 Cells with a Novel Monoclonal Anti-PAR-1 Antibody (Mab COR7-6H9), J. Neurocytol. 27:661-666 (1998) ("Kaufmann et al. (1998)"), both of which are incorporated herein by this reference.

In Brass et al. (1992), monoclonal antibodies were prepared against the immunogen SFLLRNPNDKYEPF (SEQ ID NO: 1) which represents residues 42-55 of human PAR1. These monoclonal antibodies were prepared by standard techniques, beginning with the immunization of mice with the immunogen SFLLRNPNDKYEPF (SEQ ID NO: 1) conjugated to keyhole limpet hemocyanin (KLH). These monoclonal antibodies include:

(1) a monoclonal antibody designated ATAP2 in Brass et al. (1992), which binds to a first fragment of the immunogen, specifically SFLLRNPND (SEQ ID NO: 2);

(2) a monoclonal antibody designated ATAP 120 in Brass et al. (1992), which binds to a second fragment of the immunogen, specifically NPNDKYEPF (SEQ ID NO: 3); and a monoclonal antibody designated ATAP138 in Brass et al., which also binds to NPNDKYEPF (SEQ ID NO: 3).

Additionally, monoclonal antibodies usable in compositions and methods according to the present invention include monoclonal antibodies that specifically bind either or both of SFLLRNPND (SEQ ID NO: 2) or NPNDKYEPF (SEQ ID NO: 2) such that these antibodies have an affinity for either or both of SFLLRNPND (SEQ ID NO: 2) or NPNDKYEPF (SEQ ID NO: 3) that is at least 80% as great as any of ATAP2, ATAP20, or ATAP138, as measured by the reciprocal of the dissociation constant for the antibody-antigen complex.

Additionally, monoclonal antibodies usable in compositions and methods according to the present invention include monoclonal antibodies that have complementary-determining regions that are identical to those of ATAP2, ATAP20, or ATAP138. Additionally, monoclonal antibodies usable in compositions and methods according to the present invention include monoclonal antibodies that have complementary-determining regions that are identical to the monoclonal antibodies described above that specifically bind either or both of SFLLRNPND (SEQ ID NO: 2) or NPNDKYEPF (SEQ ID NO: 3) or such that these antibodies have an affinity for either or both of SFLLRNPND (SEQ ID NO: 2 or NPNDKYEPF (SEQ ID NO: 3) that is at least 80% as great as any of ATAP2, ATAP20, or ATAP138.

Kaufmann et al. (1998) described monoclonal antibodies to rat PAR1 receptor that were prepared by using a peptide with the sequence GRAVYLNKSRFPPMPPPPFISEDASG (SEQ ID NO: 4). This sequence is described as being below the thrombin cleavage site for the receptor. Analogous antibodies can be prepared against the corresponding region of human PAR1 receptor. In general, antibodies according to the present invention can be of any class, such as IgG, IgA, IgD1 IgE1 IgM1 or IgY1 although IgG antibodies are typically preferred. Antibodies can be of any mammalian or avian origin, including human, murine (mouse or rat, donkey, sheep, goat, rabbit, camel, horse, or chicken. In some alternatives, the antibodies can be bispecific. The antibodies can be modified by the covalent attachment of any type of molecule to the antibody. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, or other modifications known in the art. Monoclonal antibodies can be prepared using a wide variety of techniques known in the art including the use of hybridoma, recombinant, and phage display technologies, or a combination thereof.

For example, monoclonal antibodies can be produced using hybridoma techniques including those known in the art and taught, for example, in Harlow et al., "Antibodies: A Laboratory Manual", (Cold Spring Harbor Laboratory Press, 2nd ed. 1988); Hammerling, et al., in: Monoclonal Antibodies and T-Cell Hybridomas 563-681 (Elsevier, N.Y., 1981), or by other standard methods known in the art.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. For example, suitable antibodies can be produced by phage display or other techniques.

Additionally, and not by way of limitation, human antibodies can be made by a variety of techniques, including phage display methods using antibody libraries derived from human immunoglobulin sequences and by the use of transgenic mice that are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. The antibodies can also be produced by expression of polynucleotides encoding these antibodies.

Additionally, antibodies according to the present invention can be fused to marker sequences, such as a peptide tag to facilitate purification; a suitable tag is a hexahistidine tag. The antibodies can also be conjugated to a diagnostic or therapeutic agent by methods known in the art. Techniques for preparing such conjugates are well known in the art.

Other methods of preparing these monoclonal antibodies, as well as chimeric antibodies, humanized antibodies, and single-chain antibodies, are known in the art.

In addition to compounds which inhibit or suppress PAR1 biochemical or signaling activities, compounds which are capable of suppressing PAR1 expression or down-regulating PAR1 cellular levels can also be used in the practice of the present invention. Suppression of PAR1 expression or down-regulation of its cellular level refers to a decrease in or an absence of PAR1 expression in an examined cell (e.g., a cell which has been contacted with a PAR1 antagonist compound), as compared to PAR1 in a control cell (a cell not treated with the PAR1 antagonist compound). PAR1 level or expression can be decreased or reduced by at least about 10% (e.g., by 20%, 30%, 40%, 50%, 60%, 70%, 80%, or 90%, as compared to PAR1 level or expression in the control cell.

As indicated above, suppression of expression or down-regulation of PAR1 cellular levels can be carried out at either the level of transcription of the gene for PAR1 into mRNA or the translation of mRNA for PAR1 into the corresponding protein.

In some embodiments, inhibitory nucleotides are used to antagonize PAR1 mediated cardiac remodeling or other effects of PAR1 by suppressing PAR1 expression. These include short interfering RNA (siRNA), microRNA (miRNA), and synthetic hairpin RNA (shRNA), anti-sense nucleic acids, or complementary DNA (cDNA). In some preferred embodiments, a siRNA targeting PAR1 expression is used. Interference with the function and expression of endogenous genes by double-stranded RNA such as siRNA has been shown in various organisms. See, e.g., A. Fire et al., "Potent and Specific Genetic Interference by Double-Stranded RNA in Caenorhabditis elegans" Nature 391:806-811 (1998); J. R. Kennerdell & R. W. Carthew, "Use of dsDNA-Mediated Genetic Interference to Demonstrate that frizzled and frizzled 2 Act in the Wingless Pathway," CeJ 95:1017-1026 (1998); F. Wianni & M. Zernicka-Goetz, "Specific Interference with Gene Function by Double-Stranded RNA in Early Mouse Development," Nat. Cell Biol. 2:70-75 (2000). siRNAs can include hairpin loops comprising self-complementary sequences or double stranded sequences.

siRNAs typically have fewer than 100 base pairs and can be, e.g., about 30 bps or shorter, and can be made by approaches known in the art, including the use of complementary DNA strands or synthetic approaches. Such double-stranded RNA can be synthesized by in vitro transcription of single-stranded RNA read from both directions of a template and in vitro annealing of sense and antisense RNA strands. Double-stranded RNA targeting PAR1 can also be synthesized from a cDNA vector construct in which a PAR1 gene (e.g., human PAR1 gene) is cloned in opposing orientations separated by an inverted repeat. Following cell transfection, the RNA is transcribed and the complementary strands reanneal. Double-stranded RNA targeting the PAR1 gene can be introduced into a cell (e.g., a tumor cell) by transfection of an appropriate construct.

Typically, RNA interference mediated by siRNA, miRNA, or shRNA is mediated at the level of translation; in other words, these interfering RNA molecules prevent translation of the corresponding mRNA molecules and lead to their degradation. It is also possible that RNA interference may also operate at the level of transcription, blocking transcription of the regions of the genome corresponding to these interfering RNA molecules.

The structure and function of these interfering RNA molecules are well known in the art and are described, for example, in R. F. Gesteland et al., eds, "The RNA World" ($3^{rd}$ ed, Cold Spring Harbor Laboratory Press, Cold Spring Harbor, N.Y., 2006), pp. 535-565, incorporated herein by this reference. [0110] For these approaches, cloning into vectors and transfection methods are also well known in the art and are described, for example, in J. Sambrook & D. R. Russell, "Molecular Cloning: A Laboratory Manual" ($3^{rd}$ ed., Cold Spring Harbor Laboratory Press, Cold Spring Harbor, 2001), incorporated herein by this reference.

In addition to double stranded RNAs, other nucleic acid agents targeting PAR1 can also be employed in the practice of the present invention, e.g., antisense nucleic acids. Antisense nucleic acids are DNA or RNA molecules that are complementary to at least a portion of a specific target mRNA molecule. In the cell, the single stranded antisense molecule hybridizes to that mRNA, forming a double stranded molecule. The cell does not translate an mRNA in this double-stranded form. Therefore, antisense nucleic acids interfere with the translation of mRNA into protein, and, thus, with the expression of a gene that is transcribed into that mRNA. Antisense methods have been used to inhibit the expression of many genes in vitro. See, e.g., C J. Marcus-Sekura, "Techniques for Using Antisense Oligodeoxy ribonucleotides to Study Gene Expression," Anal. Biochem. 172:289-295 (1988); J. E. Hambor et al., "Use of an Epstein-Ban Virus Episomal Replicon for Anti-Sense RNA-Mediated Gene Inhibition in a Human Cytotoxic T-CeIl Clone," Proc. Natl. Acad. Sci. U.S.A. 85:4010-4014 (1988); H Arima et al., "Specific inhibition of lnterleukin-10 Production in Murine Macrophage-Like Cells by Phosphorothioate Antisense Oligonucleotides," Antisense Nucl. Acid Drug Dev. 8:319-327 (1998); and W.-F. Hou et al., "Effect of Antisense Oligodeoxynucleotides Directed to Individual Calmodulin Gene Transcripts on the Proliferation and Differentiation of PC12 Cells," Antisense Nucl. Acid Drug Dev. 8:295-308 (1998), all incorporated herein by this reference. Antisense technology is described further in C. Lichtenstein & W. Nellen, eds., "Antisense Technology: A Practical Approach" (IRL Press, Oxford, 1997), incorporated herein by this reference. [0111] PAR1 polynucleotide sequences from human and many other mammals have all been delineated in the art. For example, human PAR1 cDNA sequence (NM_001992) was reported in T.-K. H. Vu et al., "Molecular Cloning of a Functional Thrombin Receptor Reveals a Novel Proteolytic Mechanism of Receptor Activation," CeJ 64:1057-1068 (1991), incorporated herein by this reference. Based on the known sequences, inhibitory nucleotides (e.g., siRNA, miRNA, or shRNA) targeting PAR1 can be readily synthesized using methods well known in the art.

Exemplary siRNAs according to the invention could have up to 29 bps, 25 bps, 22 bps, 21 bps, 20 bps, 15 bps, 10 bps, 5 bps or any integral number of base pairs between these numbers. Tools for designing optimal inhibitory siRNAs include that available from DNAengine Inc. (Seattle, Wash.) and Ambion, Inc. (Austin, Tex.). Specific PAR1 inhibitory nucleotides and their use in down-regulating PAR1 expression have also been disclosed in the art, e.g., Q. Fang et al., "Thrombin Induces Collagen Gel Contraction Partially Through PAR1 Activation and PKC-[epsilon]," Eur. Respir. J. 24:918-924 (2004); and Y.-J. Yin et al., "Mammary Gland Tissue Targeted Overexpression of Human Protease-Activated Receptor 1 Reveals a Novel Link to [beta]-Catenin Stabilization," Cancer Res. 66:5224-5233 (2006), both incorporated herein by this reference.

Other Exemplary PAR1 antagonist that are contemplated by the invention include but are not limited to those described in U.S. Pat. No. 6,017,890 (Hoekstra et al.: "Azole Peptidomimetics as Thrombin Receptor Antagonists"), which is herein incorporated by reference in its entirety, and is specifically incorporated by reference for its teachings of compounds that function as thrombin receptor antagonists (see, e. g., column 2, line 31, through end of column 3 and Examples 1-10).

U.S. Pat. No. 5,446,131 (to Maraganore: "Thrombin Receptor Antagonists"), which is herein incorporated by reference in its entirety, and is specifically incorporated by reference for its teachings of compounds that function as thrombin receptor antagonists (see, e. g., the Abstract and the Claims).

U.S. Pat. No. 5,866,681 (to Scarborough: "Thrombin Receptor Antagonists"), which is herein incorporated by reference in its entirety, and is specifically incorporated by reference for its teachings of compounds that function as thrombin receptor antagonists (see, e. g., the Abstract, the Claims, and Examples 1-16).

U.S. Pat. No. 5,759,994 (to Coughlin: "Recombinant Thrombin Receptor and Related Pharmaceuticals"), which is herein incorporated by reference in its entirety, and is specifically incorporated by reference for its teachings of compounds that function as thrombin receptor antagonists (see, e. g., Examples 5 and 6, and the Claims).

U.S. Pat. No. 5,798,248 (to Coughlin: "Recombinant Thrombin Receptor and Related Pharmaceuticals"), which is herein incorporated by reference in its entirety, and is specifically incorporated by reference for its teachings of compounds that function as thrombin receptor antagonists (see, e. g., Examples 5 and 6, and the Claims).

in Bernatowicz et al. ("Development of Potent Thrombin Receptor Antagonists." J. Mecl. Chem. 39: 4879-4887, 1996), which is herein incorporated by reference in its entirety, and is specifically incorporated by reference for its teachings of compounds that function as thrombin receptor antagonists (see, e. g., Tables 1-8).

Vassollo et al. ("Structure-Function Relationships in the Activation of Platelet Thrombin Receptors by Receptor-Derived Peptides." J. Biol. Chem. 267: 6081-6085, 1992), which is herein incorporated by reference in its entirety, and is specifically incorporated by reference for its teachings of compounds that function as thrombin receptor antagonists (see, e.g., Table I).

Andrade-Gordon et al. ("Design, Synthesis, and Biological Characterization of a Peptide-Mimetic Antagonist for a Tethered-Ligand Receptor." Proc. Natl. Acad. Sci. USA 96: 12257-12262, 1999), which is herein incorporated by reference in its entirety, and is specifically incorporated by reference for its teachings of compounds that function as thrombin receptor antagonists (see, e.g., FIG. 1).

Hoekstra et al. ("Thrombin Receptor (PAR-1) Antagonists. Heterocycle-Based Peptidomimetics of the SFLLR Agonist Motif." Bioorg. Med. Chem. Lett. 8: 1649-1654, 1998), which is herein incorporated by reference in its entirety, and is specifically incorporated by reference for its teachings of compounds that function as thrombin receptor antagonists (see, e. g., Tables 1 and 2).

Kato et al. ("In Vitro Antiplatelet Profile of FR171113, a Novel Non-Peptide Thrombin Receptor Antagonist." Euro. J. Pharmacol. 384: 197-202, 1999), which is herein incorporated by reference in its entirety, and is specifically incorporated by reference for its teachings of compounds that function as thrombin receptor antagonists (see, e. g., FIG. 1).

Ruda et al. ("Identification of Small Peptide Analogues Having Agonist and Antagonist Activity at the Platelet Thrombin Receptor." Biochem. Pharmacol. 37: 2417-2426, 1988), which is herein incorporated by reference in its entirety, and is specifically incorporated by reference for its teachings of compounds that function as thrombin receptor antagonists (see, e. g., the Abstract and FIG. 1).

Ruda et al. ("Thrombin Receptor Antagonists: Structure-Activity Relationships for the Platelet Thrombin Receptor and Effects on Prostacyclin Synthesis by Human Umbilical Vein Endothelial Cells." Biochem. Pharmacol. 39: 373-381, 1990), which is herein incorporated by reference in its entirety, and is specifically incorporated by reference for its teachings of compounds that function as thrombin receptor antagonists (see, e. g., Table 2).

Harmon and Jamieson ("Activation of Platelets by Alpha-Thrombin is a Receptor-Mediated Event." J. Biol. Chem. 261: 15928-15933, 1986), which is herein incorporated by reference in its entirety, and is specifically incorporated by reference for its teachings of compounds that function as thrombin receptor antagonists (see, e. g., the abstract at page 15928, left column).

Figure 3:
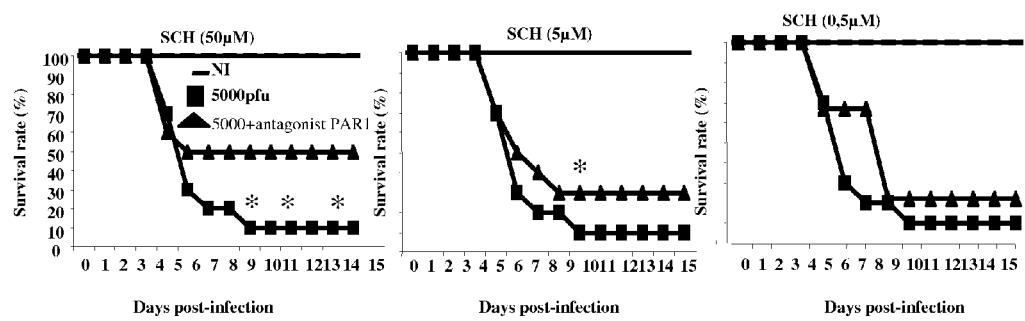
FIGS. 3 A and B: PAR1 antagonist SCH79797 protects mice from IAV induced-death in a dose-reponse dependant manner (A and after infection with different pfu/mice (B.

Doorbar and Winter ("Isolation of a Peptide Antagonist to the Thrombin Receptor Using Phage Display." J. Mol. Biol. 244: 361369, 1994), which is herein incorporated by reference in its entirety, and is specifically incorporated by reference for its teachings of compounds that function as thrombin receptor antagonists (see, e. g., FIG. 3).

Ahn et al. ("Structure-Activity Relationships of Pyrroloquinazolines as Thrombin Receptor Antagonists." Bioorg. Med. Chem. Lett. 9: 2073-2078, 1999), which is herein incorporated by reference in its entirety, and is specifically incorporated by reference for its teachings of compounds that function as thrombin receptor antagonists (see, e. g., Tables 1 and 2).

Seiler et al. ("Inhibition of Thrombin and SFLLR-Peptide Stimulation of Platelet Aggregation, Phosphlipase A2 and Na+/H+ Exchange by a Thrombin Receptor Antagonist." Biochem. Pharmacol. 49: 519-528, 1995), which is herein incorporated by reference in its entirety, and is specifically incorporated by reference for its teachings of compounds that function as thrombin receptor antagonists (see, e. g., the Abstract).

Elliot et al. ("Photoactivatable Peptides Based on BMS-197525: A Potent Antagonist of the Human Thrombin Receptor (PAR-1)." Bioorg. Med. Chem. Lett. 9: 279-284, 1999), which is herein incorporated by reference in its entirety, and is specifically incorporated by reference for its teachings of compounds that function as thrombin receptor antagonists (see, e. g., Table 1).

Fujita et al. ("A Novel Molecular Design of Thrombin Receptor Antagonists." Bioorg. Med. Chem. Lett. 9: 1351-1356, 1999), which is herein incorporated by reference in its entirety, and is specifically incorporated by reference for its teachings of compounds that function as thrombin receptor antagonists (see, e. g., the Abstract).

Debeir et al. ("Pharmacological Characterization of Protease-Activated Receptor (PAR-1) in Rat Astrocytes." Euro. J. Pharmacol. 323: 111-117, 1997), which is herein incorporated by reference in its entirety, and is specifically incorporated by reference for its teachings of compounds that function as thrombin receptor antagonists (see, e. g., the Abstract).

Ahn et al. ("Binding of a Thrombin Receptor Tethered Ligand Analogue to Human Platelet Thrombin Receptor." Mol. Pharmacol. 51: 350356, 1997), which is herein incorporated by reference in its entirety, and is specifically incorporated by reference for its teachings of compounds that function as thrombin receptor antagonists (see, e. g., FIG. 5 and Table 1).

McComsey et al. ("Heterocycle-peptide hybrid compounds. Aminotriazole-containing agonists of the thrombin receptor (PAR-1)." Bioorganic & Medicinal Chemistry Letters 9: 1423-1428, 1999), which is herein incorporated by reference in its entirety, and is specifically incorporated by reference for its teachings of compounds that function as thrombin receptor antagonists (see, e. g., Table: Biological Data).

Nantermet et al. ("Discovery of a small molecule antagonist of the human platelet thrombin receptor (PAR-1)." Bioorganic & Medicinal Chemistry Letters 12: 319-323, 2002, which is herein incorporated by reference in its entirety, and is specifically incorporated by reference for its teachings of compounds that function as thrombin receptor antagonists (see, e. g., Table 1, Table 2, Table 3).

Barrow et al. ("Discovery and initial structure-activity relationship of trisubstituted ureas as thrombin receptor (PAR-1) antagonists." Bioorganic & Medicinal Chemistry Letters 11: 2691-2696, 2001), which is herein incorporated by reference in its entirety, and is specifically incorporated by reference for its teachings of compounds that function as thrombin receptor antagonists (see, e. g., Table 1-5).

Ahn et al. ("Inhibition of cellular action of thrombin by N3-cyclopropyl-7 [[4-(1-methylethyl phenyl]methyl]-7H-pyrrole[3,2f]quinazoline1,3-diamine (SCH79797), a non-peptide thrombin receptor antagonist." Biochemical Pharmacol 60: 1425-1434, 2000, which is herein incorporated by reference in its entirety, and is specifically incorporated by reference for its teachings of compounds that function as thrombin receptor antagonists (see, e. g., FIG. 1).

Chackalamannil ("Thrombin receptor antagonists as novel therapeutic targets." Curr Opin Drug Discovery Development 4: 417-427, 2001), which is herein incorporated by reference in its entirety, and is specifically incorporated by reference for its teachings of compounds that function as thrombin receptor antagonists.

Stead et al. ("Eryloside F, a novel penasterol disaccharide possessing potent thrombin receptor antagonist activity." Bioorg. Mecl. Chem. Lett. 10: 661-664, 2000), which is herein incorporated by reference in its entirety, and is specifically incorporated by reference for its teachings of compounds that function as thrombin receptor antagonists (see, e.g., FIG. 1).

Pakala et al. ("A peptide analogue of thrombin receptor-activating peptide inhibits thrombin and thrombin-receptor-activating peptide induced vascular smooth muscle cell proliferation." J. Cardiovasc. Pharmacol. 37: 619-629, 2001), which is herein incorporated by reference in its entirety, and is specifically incorporated by reference for its teachings of compounds that function as thrombin receptor antagonists (see, e. g., FIGS. 1 and 2).

Zhang et al. ("Discovery and optimization of a novel series of thrombin receptor (PAR-1) antagonists: potent, selective peptide mimetics based on indole and indazole templates." J. Med. Chem. 44: 1021-1024, 2001), which is herein incorporated by reference in its entirety, and is specifically incorporated by reference for its teachings of compounds that function as thrombin receptor antagonists.

A further object of the invention relates a method for screening a PAR1 antagonist for use in the treatment or prevention of a influenza virus type A infection. For example, the screening method may measure the binding of a candidate compound to PAR1, or to cells or membranes bearing PAR1, or a fusion protein thereof by means of a label directly or indirectly associated with the candidate compound. Furthermore, the screening method may involve measuring or, qualitatively or quantitatively, detecting ability of said candidate compound to inactivate PAR1.

In a particular embodiment, the screening method of the invention comprises the step consisting of:

a) providing a plurality of cells expressing PAR1 on their surface:

b) incubating said cells with a candidate compound;

c) determining whether said candidate compound binds to and inactivates PAR1; and d) selecting the candidate compound that binds to and inactivates PAR1, In a particular embodiment, the screening method of the invention may further comprising a step consisting of administering the candidate compound selected at step d) to an animal model of influenza virus type A infection to validate the protective effects of said candidate compound.

In general, such screening methods involve providing appropriate cells which express PAR1 on their surface. In particular, a nucleic acid encoding PAR1 may be employed to transfect cells to thereby express the receptor of the invention. Such a transfection may be accomplished by methods well known in the art. In a particular embodiment, said cells may be selected from the group consisting of the mammal cells reported yet to express PAR1 (e.g. epithelial cells).

The screening method of the invention may be employed for determining a PAR1 antagonist by contacting such cells with compounds to be screened and determining whether such compound inactivates PAR1.

According to a one embodiment of the invention, the candidate compounds may be selected from a library of compounds previously synthesised, or a library of compounds for which the structure is determined in a database, or from a library of compounds that have been synthesised de novo or natural compounds. The candidate compound may be selected from the group of (a) proteins or peptides, (b) nucleic acids and (c) organic or chemical compounds (natural or not).

PAR1 inactivation with the candidate compound can be tested by various known methods of the man skilled in the art.

Another object of the invention relates to a method for treating or preventing a influenza virus type A infection comprising administering a subject in need thereof with an PAR1 antagonist.

As used herein, the term "subject" denotes a mammal, such as a pig and a primate. Preferably, a subject according to the invention is a human.

PAR1 antagonists may be administered in the form of a pharmaceutical composition, as defined below.

Preferably, the PAR1 antagonist of the invention is administered in a therapeutically effective amount. By a "therapeutically effective amount" is meant a sufficient amount the PAR1 antagonist according to the invention to treat or prevent influenza virus type A infections at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the deficit being treated and the severity of the deficit; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved.

However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The PAR1 antagonist may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Preferably, the pharmaceutical composition according to the invention in preferably administered in an intranasal administration form.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action pf microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The PAR1 antagonist can be formulated into a composition in a neutral or salt form. Pharmaceutically acceptable salts include the acid addition salts (formed with the free amine groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The PAR1 antagonist may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

According to the present invention, the PAR1 antagonist may be formulated in combinations with one or more distinct active pharmaceutical agents, preferably active pharmaceutical agents for the treatment of influenza virus type A infection. Such agents may act by very different biochemical pathways to provide particularly beneficial therapeutic results.

According to the present invention the one or more active agents may be delivered as either co-administered monotherapy formulations, or as a single co-formulation.

In a preferred embodiment, one of the active agents is a PAR2 agonist.

A further object of the invention relates to a pharmaceutical composition comprising
(i) at least one PAR-1 antagonist, and
(ii) at least one Protease-Activated Receptors-2 (PAR-2) agonist.

A further object of the invention relates to the Use of said pharmaceutical composition for the treatment or prevention of an influenza virus type A infection in a subject.

A further object of the invention relates to products containing:
(i) at least one PAR-1 antagonist, and
(ii) at least one Protease-Activated Receptors-2 (PAR-2) agonist,
as a combined preparation for simultaneous, separate, or sequential use for the treatment or prevention of an influenza virus type A infection in a subject.

As used herein, the term "PAR2" has its general meaning in the art and refers to Protease-Activated Receptor-2. The term may include naturally occurring PAR2 and variants and modified forms thereof. The PAR2 can be from any source, but typically is a mammalian (e.g., human and non-human primate) PAR2, particularly a human PAR2, As used herein the term "PAR2 agonist" is n natural or synthetic compound which binds and activates PAR2 for initiating a pathway signalling and further biological processes. PAR-2 agonistic activity may assessed by various known methods. For example, the Hollenberg's method (Hollenberg, M. D., et al., Cati. J. Physiol. Pharmacol., 75, 832-841 (1997)), the Kawabata's method (Kawabata, A., et al., J. Pharmacol. Exp. Ther., 288, 358-370 (1999)) and the Hawthorne's method (Howthorne et al., A High-Throughput Microtiter Plate-Based Calcium Assay for the Study Of Protease-Activated Receptor 2 Activation, Analytical Biochemistry 290, 378-379 (2001)) may be used for assessing a PAR2 agonistic activity.

In one embodiment, a PAR2 agonist according to the invention may be a small organic molecule. Exemplary PAR2 agonists that are contemplated by the invention include but are not limited to those described in U.S. Patent Application Publications Nos. 2007123508 and 2008318960 that are hereby incorporated by reference into the present disclosure. Other examples include those described in Graddil L R et al. 2008, and more particularly AC-55541 [N-[[1-(3-bromophenyl)-cth-(E)-ylidene-hydrazinocarbonyi}-(4-oxo-3,4-dihydro-phthalazin-1-yI)-methylj-benzamide] and AC-264613 [2-oxo-4-phenyipyrrolidine-3-carboxylic acid [t(3-bromophenyl-(E/Z)-ethylidene}-hydrazide].

In another embodiment, a PAR2 agonist according to the invention is a PAR2 activating peptide that may be HOOC-SLIGRL-NH2 (SEQ ID NO: 5) or HOOC-SLIGKV-NH2 (SEQ ID NO: 6).

In another embodiment a PAR2 agonist of the invention may be a PAR2 activating peptide derivative that may be selected from the group consisting of HOOC-LIGRLO-NH2, HOOC-Fluoryi-LIGRLO-NH2, and trans-cinnamoyl-LIGRLO (tc)-NH2.

Other PAR2 activating peptide derivatives that are contemplated by the invention include those described in International Patent Application Publication No W003/104268 (that is hereby incorporated by reference into the present disclosure that are represented by the generai formula (I or a salt thereof:

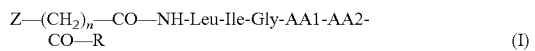

Z—(CH₂)ₙ—CO—NH-Leu-Ile-Gly-AA1-AA2-CO—R    (I)

wherein Z represents an aryl group which may or may not have a substituent or a heteroaryl group which may or may not have a substituent; n represents 0, 1 or 2; AA1-AA2 represents Lys-Val or Arg-Leu; and R represents —OH or —NH2.

The aryl group as Z may be a carbon cyclic group of mono-ring type, multi-ring type or condensed ring type, with 6 to 30 carbon atoms, preferably 6 to 14 carbon atoms, specifically including for example phenyl group and naphthyl group, preferably. The heteroaryl group as Z may be a heterocyclic group of 5- to 7-membered mono-ring type, multi-ring type or condensed ring type, the group containing at least one to 3 nitrogen atoms, oxygen atoms or sulfur atoms within die ring and specifically including for example furyl group, thienyl group, pyridyl group or quinolyl group, preferably.

The aryl group or heteroaryl group as Z may or may not have a substituent, which includes but is not limited to any aryl group or heteroaryl group with no adverse effects on the activity of die inventive peptide derivative, specifically including for example a halogen atom, a lower alkyl group, a lower alkoxyl group, phenyl group, a phenyl-lower alkyl group, nitre group, amino group, hydroxyl group, and carboxyl group.

The halogen atom includes for example chlorine atom, fluorine atom, and bromine atom. The lower alkyl group is preferably n linear or branched lower alkyl group with one to 15 carbon atoms, preferably one to 6 carbon atoms, which includes for example methyl group and ethyl group. The lower alkoxyl group preferably includes a linear or branched lower alkoxyl group with one to 15 carbon atoms, preferably one to 6 carbon atoms, which includes for example methoxyl group and ethoxyl group.

The lower alkyl group in the phenyl-lower alkyl group includes alkylene groups including the lower alkyl group, for example methylene group and ethylene group.

Substituents for this lower alkyl group, tower alkoxyl group, phenyl group, and phenyl-lower alkyl group may additionally be substituted with a halogen atom and the like.

The group Z in the general formula (I) in accordance with the invention includes for example substituted or unsubstituted phenyl group, naphthyl group, furyl group, thienyl group, pyridyl group and quinolyl group, specifically including for example phenyl group, 4-methoxyphenyl group, 3-methoxyphenyl group, 2-methoxyphenyl group, 2,4-dimethoxyphenyi group, 3,5-dimethoxyphenyl group, 4-phenethylphenyl group, 3-phenethylphenyl group, 2-phenethylphenyl group, 4-nitrophenyl group, 3-nitrophenyl group, 2-nitrophenyl group, 2,4-dinitrophenyl group, 3,4-dinitrophenyî group, 4-methylphenyl group, 3-methylphenyt group, 2-methyiphenyi group, 2,4-dimethylphenyl group, 3,5-dimethylphenyl group, 4-fluorophenyl group, 3-fluorophenyl group, 2-fluorophenyl group, 2,4-difluorophenyl group, 3,5-difluorophenyl group, 2,4,5-trifluorophenyl group, 4-phenylphenyl group, 3-phenylphenyl group, 2-phenylphenyl group, 2.-furyt group, 3 . . . furyl group, 5-methoxy-2-furylgroup, 5-methyl-2-furylgroup, 1-naphthyl group, 2-naphthyl group, 4-methoxy-I-naphthyl group, 4-methyl-1-naphthyl group, 4-methoxy-2-naphthyl group, 4-methyl-2-naphtyl group, 4-pyridyl group, 2-pyridyi group, 3-pyridyl group, 2-methyl-.4-pyridyl group, 4-methyl-2-pyridyl group, 2-thienyl group, 3-thienyl group, 3-methyl-2-thienyl group, 4-methyl-2-thienyl group, 4-methyl-3-thienyl group, 6-quinolyl group, 7-quinotyt group, 8-quinolyl group, 4-quinolyl group, 4-methyl-6-quinolyl group and the like, In the general formula (I), in accordance with the invention, n represents 0, 1 or 2 and the group with the inferior letter "n" is bound to the group Z. When n is 0, the group Z in directly bound to carbonyl group; when n is t, the group z is bound through methylene group to carbonyl group; and when n is 2, the group Z is bound through ethylene group to carbonyl group.

R in the general formula (I) represents —OH or —NH₂, or the salt thereof.

In accordance with the invention, AA1-AA2 in the general formula (I) represents two types of amino acids bound together. The amino acid AA1, is preferably Lys or Arg, while AA2 in preferably Val or Leu. AA1 and AA2 are bound together in the sequence AA1-AA2 along the N-terminal to C-terminal direction. Preferably AA1-AA2 includes Lys-Val or Arg-Leu, In another embodiment, a PAR2 agonist according to the invention is a protease that is known to activate PAR2. For example, trypsin and tryptase are the principal agonists of PAR2. Trypsin and tryptase cleave PAR2 to expose the tethered ligand SLIGRL (SEQ ID NO: 1) (rat and mouse PAR2), which then binds to conserved regions in extracellular loop II of the cleaved receptor. Certain coagulation factors can also activate PAR2 such as Factor VIIa or Factor Xa. Other examples include protease derived from epithelial cells such as maptriptase, human airway trypsin-like protease, and extra pancreatic tryptic enzymes.

In another embodiment the PAR2 agonist may consist in an antibody (the term including antibody fragment). In particular, the PAR2 agonist may consist in an antibody directed against the PAR2 in such a way that said antibody activates the receptor.

In another embodiment die PAR2 agonist may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then after raising aptamers directed against PAR2 as above described, the skilled man in the art can easily select those activating PAR2.

Another aspect of the invention relates to a PAR1 antagonist for inhibiting replication of an influenza virus type A.

A further object of the invention relates to a method of testing whether a subject is predisposed to an influenza virus type A infection, which comprises the step of analyzing a biological sample from said subject for:

(i) detecting the presence of a mutation in the PAR1 gene and/or its associated promoter, and/or (ii) analyzing the expression of the PAR1 gene, As used herein, the term "biological sample" refers to any sample from a subject such as blood or serum.

Typical techniques for detecting a mutation in the PAR1 gene may include restriction fragment length polymorphism, hybridisation techniques, DNA sequencing, exonuclease resistance, microsequencing, solid phase extension using ddNTPs, extension in solution using ddNTPs, oligonucleotide assays, methods for detecting single nucleotide polymorphism such as dynamic allele-specific hybridisation. ligation chain reaction, mini-sequencing, DNA "chips", allele-specific oligonucleotide hybridisation with single or dual-labelled probes merged with PCR or with molecular beacons, and others.

Analyzing the expression of the PAR1 gene may be assessed by any of a wide variety of well-known methods for detecting expression of a transcribed nucleic acid or translated protein.

In a preferred embodiment, the expression of the PAR1 gene is assessed by analyzing the expression of mRNA transcript or mRNA precursors, such as nascent RNA, of said gene. Said analysis can be assessed by preparing mRNA/cDNA from cells in a biological sample from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TaqMan), and probes arrays such as GeneChip™ DNA Arrays (AFF YMETRIX).

Advantageously, the analysis of the expression level of mRNA transcribed from the PAR1 gene involves the process of nucleic acid amplification, e.g., by RT-PCR (the experimental embodiment set forth in U.S. Pat. No. 4,683,202), ligase chain reaction (BARANY, Proc. Natl. Acad. Sci. USA, vol. 88, p: 189-193, 1991), self sustained sequence replication (GUATELLI et al., Proc. Natl. Acad. Sci. USA, vol. 57, p: 1874-1878, 1990, transcriptional amplification system (KWOH et al., 1989, Proc. Natl. Acad. Sci. USA, vol. 86, p: 1173-1177, 1989), Q-Beta Replicase (LIZARDI et al., Biol. Technology, vol. 6, p: 1197, 1988), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

In another preferred embodiment, the expression of the PAR1 gene is assessed by analyzing the expression of the protein translated from said gene. Said analysis can be assessed using an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotinstreptavidin)), or an antibody fragment (e.g., a single-chain antibody, an isolated antibody hypervariable domain, etc.) which binds specifically to the protein translated from the PAR1 gene.

Said analysis can be assessed by a variety of techniques well known from one of skill in the art including, but not limited to, enzyme immunoassay (EIA), radioimmunoassay (RIA), Western blot analysis and enzyme linked immunoabsorbant assay (RIA).

The method of the invention may comprise comparing the level of expression of the PAR2 gene in a biological sample from a subject with the normal expression level of said gene in a control. A significantly higher level of expression of said gene in the biological sample of a subject as compared to the normal expression level is an indication that the patient is predisposed to developing an influenza virus type A infection. The "normal" level of expression of the PAR2 gene is the level of expression of said gene in a biological sample of a subject not afflicted by any influenza virus type A infection. Preferably, said normal level of expression is assessed in a control sample (e.g., sample from a healthy subject, which is not afflicted by any influenza virus type A infection) and preferably, the average expression level of said gene in several control samples.

According to the present invention, the treatment or prevention of influenza virus type A infection in a subject is not the treatment or prevention of respiratory distress syndrome.

The invention will be further illustrated by the following figures and examples. However, these examples and figures should not be interpreted in any way as limiting the scope of the present invention.

EXAMPLES

Materials and Methods

Animals

Female wild-type C57BL6 mice (Charles River, Rhône, France) were used in these studies. All mice were 5 wk of age at the time of reception and were allowed to acclimatize to these conditions for 7 days before inclusion in experiments and were allowed free access to tap water and standard lab chow. Mice were kept under appropriate conditions (constant photoperiod, 12:12-h light-dark cycle, 22° C. at the Institut National de la Recherche Agronomique (INRA) animal care facilities (Jouy-en-Josas, France). All procedures involving the mice were conducted under the authority of license issued by the direction des Services Vétérinaires (accreditation N°. 78-114).

Epithelial Cells and Virus Strains

The human alveolar type II (A549) and the Madin-Darby canine kidney cell lines (MDCK) used in this study were obtained from the American Type Culture Collection and were grown respectively in MEME (10% SVF, PS, Glutamine) and MEME (5% SVF, PS, Glutamine). The IAV A/PR/8/34 (H1N1) a gift from G. F. Rimmelzwaan (Erasmus Medical Center, Rotterdam, Netherlands) was grown and produced as previously described (F. LeBouder and al, 2008; K. Khoufache and al, 2009).

Drugs Employed

The PAR1-agonist peptide TFLLR-NH2 (H-Thr-Phe-Leu-Leu-Arg-NH2, SEQ ID N°7) and the control peptide FTLLR-NH2 (H-Phe-Thr-Leu-Leu-Arg-NH2, SEQ ID N°8) were purchased from BACHEM Switzerland (Bubendorf, Switzerland). The PAR-1 antagonist SCH79797 dihydrochloride was purchased from AXON MEDCHEM Netherlands (Groningen, Netherlands).

Pretreatment of A549 with PAR1-Agonist TFLLR-NH2

Before infection with the IAV A/PR8/34 strain, A549 cells were stimulated or not for 5 mn with 250 µM PAR1-specific activating peptide TFLLR-NH2. The amount of RANTES, IL-6 and IL-8 released was analyzed in the culture supernatants at 8, 24, 48 and 72 hours post-infection by ELISA (R&D Systems). Virus titers were also determined in the same supernatants by classical plaque assays.

In Vivo PAR1-Agonist TFLLR-NH2 Effect

For PAR1-agonist (TFLLR-NH2) stimulation experiments, six-week-old C57BL/6 female mice (Charles & River Laboratories) were anesthetized (IP) every day for 3 days and exposed intranasally to 25 µl of different solutions. The first day, anesthetized mice were inoculated intranasally with 25 µl solutions (5000, 500, 50 or 10 PFU of A/PR/8/34 in the presence or absence 50 µM of TFLLR-NH2 PAR-1 agonist or FTLLR-NH2 PAR-1 control). At days 2 and 3 post-infection the mice were just exposed intranasally to 25 µl of peptide only or MEME medium for the mice no treated (25 µl/mouse. Infected mice were then monitored daily for survival and weight, virus loads were determined by plaque assays, cytokines (RANTES & IL-6) and polynuclearneutrophils (PMN) were dosed in the bronchoalveolar lavage fluid (LBA) after 24 and 48 h post-infection in the lungs of sacrificed mice. Finally, in order to determine the secondary effect of PAR-1 agonist in vivo, we exposed the mice intranasally to 25 µl of PAR-1 agonist (50 µM) versus MEME medium for control mice. Treated mice were then monitored daily for survival rate and weight.

In Vivo PAR1-Antagonist SCH79797 Effect

To determine the in vivo SCH79797 protect dose, six-week-old C57BL/6 female mice (Charles & River Laboratories were anesthetized (IP every day for 3 days and exposed intranasally to 25 µl of solutions contain a variable concentrations of SCH79797 (50; 5; 0.5 and 0.2 µM and constant A/PR/8/34 pfu (5000 pfu). The first day, anesthetized mice were inoculated intranasally with 25 µl solutions (5000, PFU of A/PR/8/34) in the presence or absence 50, 5, 0.5 and 0.2 µM of SCH79797 PAR-1 antagonist. In the second and the third days post-infection the mice were just exposed intranasally to 25 µl of SCH79797 at 50, 5, 0.5 and 0.2 µM versus, equivalent MEME volume for the mice control (infected). Then, the infected mice were monitored daily for survival and weight.

In the second step and in order to determine the protection rate of SCH79797 at low IAV pfu, six-week-old C57BL/6 female mice (Charles & River Laboratories) were anesthetized (IP) every day for 3 days and exposed intranasally to 25 µl of solutions contain a variable pfu of A/PR/8/34 (5000, 500, 50 pfu) virus and constant concentrations of SCH79797 (50 µM). At second days and the third days post-treatment the animals were just exposed intranasally to 25 µl of SCH79797 at 50 µM or MEME for the mice control. Then, as described above, the infected mice were monitored daily for survival and weight, virus loads were determined by plaque assays, cytokines (RANTES & IL-6) and polynuclearneutrophils (PMN) were dosed in the bronchoalveolar lavage fluid (LBA) at 24 and 48 h post-infection in the lungs of sacrificed mice.

May-Grünewald and Giemsa Staining

Bronchoalveolar lavage fluid (BALF) was collected in PBS (Invitrogen) supplemented with 1 mM EDTA (Invitrogen). After cytocentrifugation, the percentage of polynuclear neutrophils was determined by counting a total of 500 cells per sample by microscopic examination of May-Grunwaldand Giemsa-stained cytocentrifuge Superfrost-Plus® slides.

Lung Histology

Lung tissue sections were cut from whole lungs fixed in 10% formalin and embedded in paraffin. Twelve-micrometer-thick sections were taken and stained with H&E for histopathological evaluation as previously described.

Statistical Analysis

The Mann-Whitney U test was used for statistical significance of viral replication and ELISA experiments. A Kaplan-Meier test was used for survival differences in mice. The statistical significance was noted when necessary and tested with a threshold of $p<0.05$.

Results

PAR1-Agonist TFLLR-NH2 Increase the Release of IAV Virus Replication in IAV-Infected Epithelial Cells To investigate the role of PAR1 in IAV replication, A549 alveolar epithelial cells were infected with IAV and stimulated with the selective TFLLR-NH2PAR1 agonist or a control peptide. When exposed to the PAR1 agonist, IAV infected cells subsequently produced more viruses (FIG. 1A) compared with cells that were exposed to the inactive control peptide. We concluded that PAR1 activation leads to increased virus production in A549-infected cells.

Figures 1B, 1C, 1D:
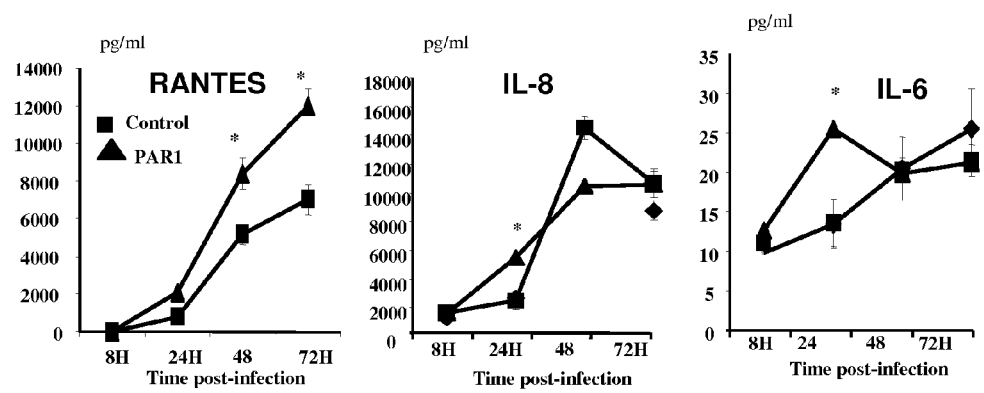
Figure 2A:
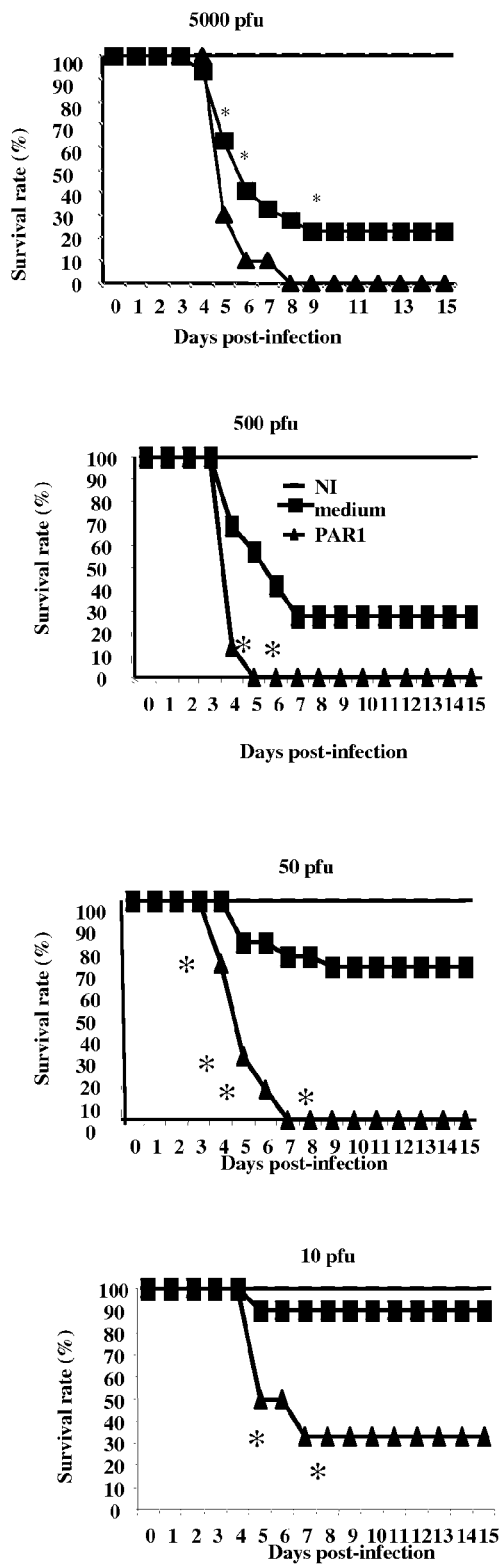
FIGS. 2 A and B: PAR1 agonist peptide increase IAV induced-death in mice in a specific dependent manner A—Survival rate of infected mices treated or not with PAR1-agonist TFLLR-NH2. B—Survival rate and weight (% of initial weight) of non-infected mices treated or not with PAR1-agonist TFLLR-NH2: the PAR1 agonist peptide has no side effect in non infected mice.
Figure 2B:
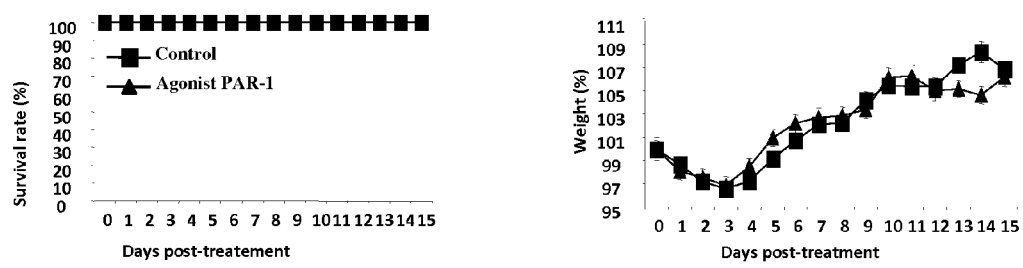
Figure 2C:
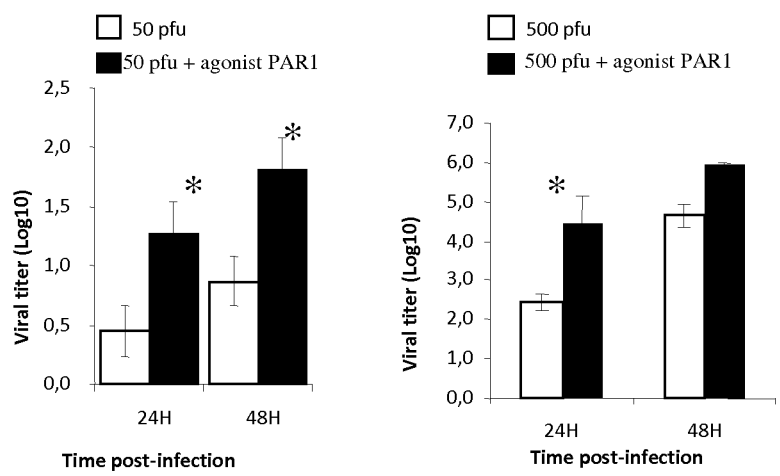

We then investigated the effect of PAR1 activation on the release of inflammatory cytokines in lung epithelial cells infected with IAV. Stimulation of PAR1 in those cells significantly increased RANTES, IL-8 and IL-6 release (FIGS. 1B, C, D). Thus, an agonist of PAR1 influences cytokine release in A549-IAV-infected-cells.

PAR1-Agonist TFLLR-NH2 Increase Pathogenesis and Death in Vivo

To investigate the role of PAR1 in vivo, mice were infected intranasally with different doses of IAV (5000, 500, 50 and 10 pfu/mice) and stimulated or not with 50 µM of PAR1 agonist peptide. Results showed that treatment with the PAR1 agonist increased IAV-induced death in mice compared to non stimulated mice (FIG. 2A. This increased was not due to a side effect of PAR1 since uninfected mice were not sensitive to PAR1 agonists (FIG. 2B. This increased pathogenesis in IAV-infected mice by PAR1 agonist led us to further investigate whether PAR1 agonist might regulate the replication of IAV in vivo. Viral load was thus evaluated in the lungs of infected mice stimulated or not with the PAR1 agonist 24 and 48 hours post-infection. Results showed that infected mice that were treated with the PAR1 specific agonist had significantly increased infectious virus loads in their lungs compared with infected mice that were not stimulated (FIG. 2C. This was observed at two different pfu/mice. Thus, PAR1 agonist increases IAV replication in vivo.

Protection From IAV Induced Pathogenesis and Death by the PAR1 Antagonist SCH79797

Figure 3B:
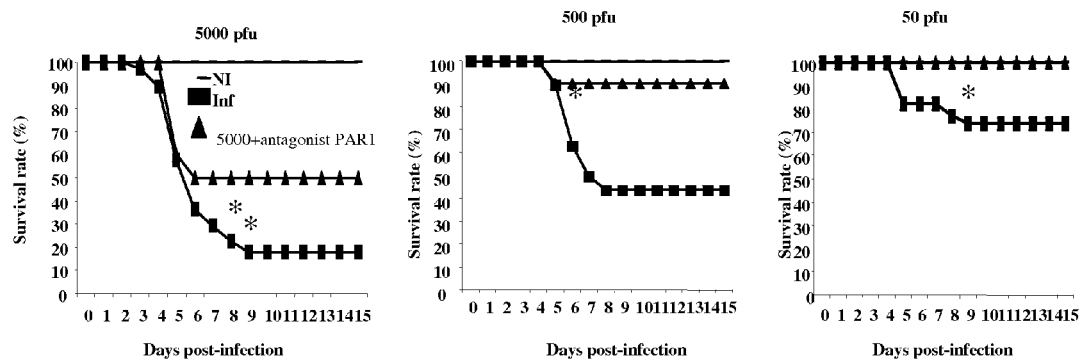
Figure 3C:
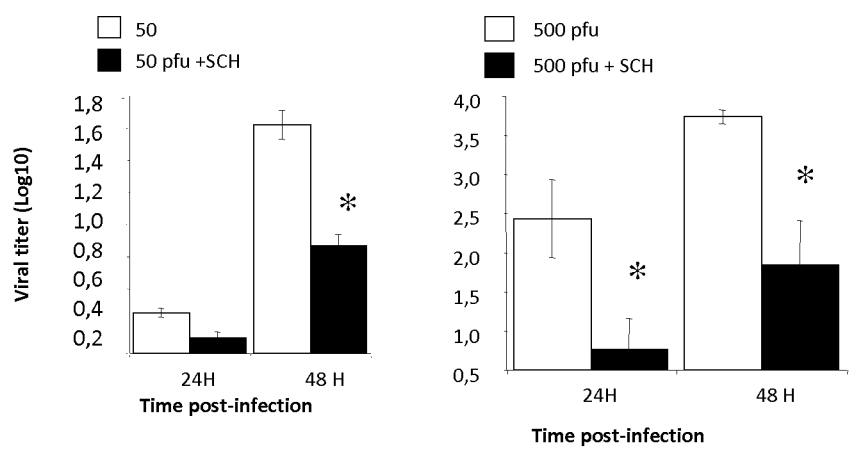

To investigate the role of PAR1 antagonist in vivo, mice were infected intranasally with 5000 pfu/mice and treated with different concentrations of the PAR1 antagonist SCH79797. Results showed that treatments with the PAR1 antagonist protected mice from IAV induced death in a dose-dependent manner (FIG. 3A). In addition, 50 μM of the antagonist PAR1 protected mice from IAV-induced death after infection with different pfu/mice, ie: 5000, 500 and 50 (FIG. 3B). We thus conclude that PAR1 antagonist protected mice from IAV-induced death in mice. Finally, viral load was evaluated in the lungs of infected mice stimulated or not with the PAR1 antagonist 24 and 48 hours post-infection. Results showed that infected mice who have been treated with the specific antagonist of PAR1 have significantly decreased infectious virus load in their lungs compared to untreated mice (FIG. 3C). Thus, the PAR1 antagonist inhibits virus replication and protects from IAV induced-pathogenesis and death in mice.

The invention claimed is:

1. A method of treating an influenza virus type A infection which comprises administration of a therapeutically effective amount of at least one Protease-Activated Receptor-1 (PAR-1) antagonist to a subject, wherein said at least one PAR-1 antagonist is N3-cyclopropyl-7-{[4-(1-methylethyl)phenyl]methyl}-7H-pyrrolo[3,2-f]quinazoline-1,3-diamine.

2. The method according to claim 1 wherein said influenza virus type A is H1N1 virus.

3. The method according to claim 1 wherein said subject is a mammal.

4. The method of claim 1 wherein said subject is a human.

5. The method of claim 1 further comprising administration of a therapeutically effective amount of at least one Protease-Activated Receptor-2 (PAR-2) agonist wherein the at least one PAR-1 antagonist and the at least one PAR-2 agonist are administered simultaneously, separately or sequentially to the subject.

6. The method of claim 1 wherein the therapeutically effective amount of the PAR-1 antagonist is administered in a pharmaceutical composition comprising:
(i) a therapeutically effective amount of at least one PAR-1 antagonist,
(ii) a therapeutically effective amount of at least one Protease-Activated Receptor-2 (PAR-2) agonist and a pharmaceutically acceptable carrier.

* * * * *